(12) United States Patent
Robinson

(10) Patent No.: US 6,178,552 B1
(45) Date of Patent: *Jan. 30, 2001

(54) WELDING HELMET

(76) Inventor: Steven Robinson, 1727 Van Tress Ave., Wilmington, CA (US) 90744

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/843,385

(22) Filed: Apr. 15, 1997

(51) Int. Cl.[7] .................................. A42B 3/18; A61F 9/06
(52) U.S. Cl. .................................................. 2/8; 2/9
(58) Field of Search ..................... D29/102, 106, D29/108, 110; 2/8, 9, 206, 410

(56) References Cited

U.S. PATENT DOCUMENTS

| D. 259,578 | * | 6/1981 | Carreiro | D21/190 |
|---|---|---|---|---|
| D. 308,266 | * | 5/1990 | Van Wyk | D29/15 |
| D. 308,586 | * | 6/1990 | Van Wyk | D29/15 |
| D. 330,950 | * | 11/1992 | Voepel | D29/12 |
| D. 355,053 | * | 1/1995 | Honrud | D29/110 |
| D. 382,370 | * | 8/1997 | Comstock et al. | D29/106 |
| 2,711,541 | * | 6/1955 | Bellett | 2/206 |
| 3,106,041 | * | 10/1963 | Kahn | 2/206 |
| 3,914,796 | * | 10/1975 | Barta | 2/8 |
| 4,117,554 | * | 10/1978 | Palumbo | 2/8 |

* cited by examiner

Primary Examiner—Michael A. Neas
(74) Attorney, Agent, or Firm—Lawrence S. Cohen

(57) ABSTRACT

A welding helmet of thermosetting plastic material having an exterior in the form of a mammalian head.

8 Claims, 4 Drawing Sheets

(2 of 4 Drawing Sheet(s) Filed in Color)

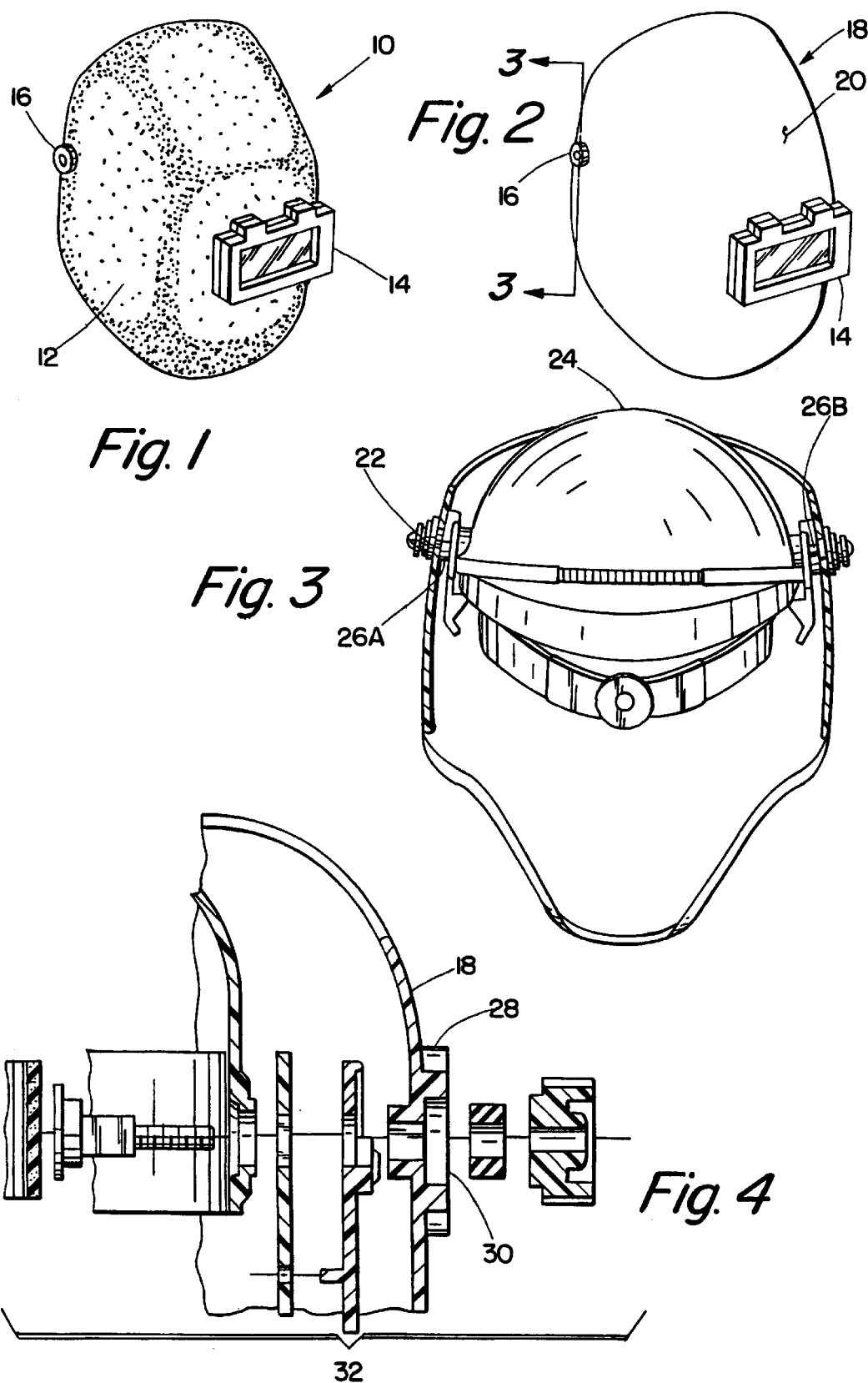

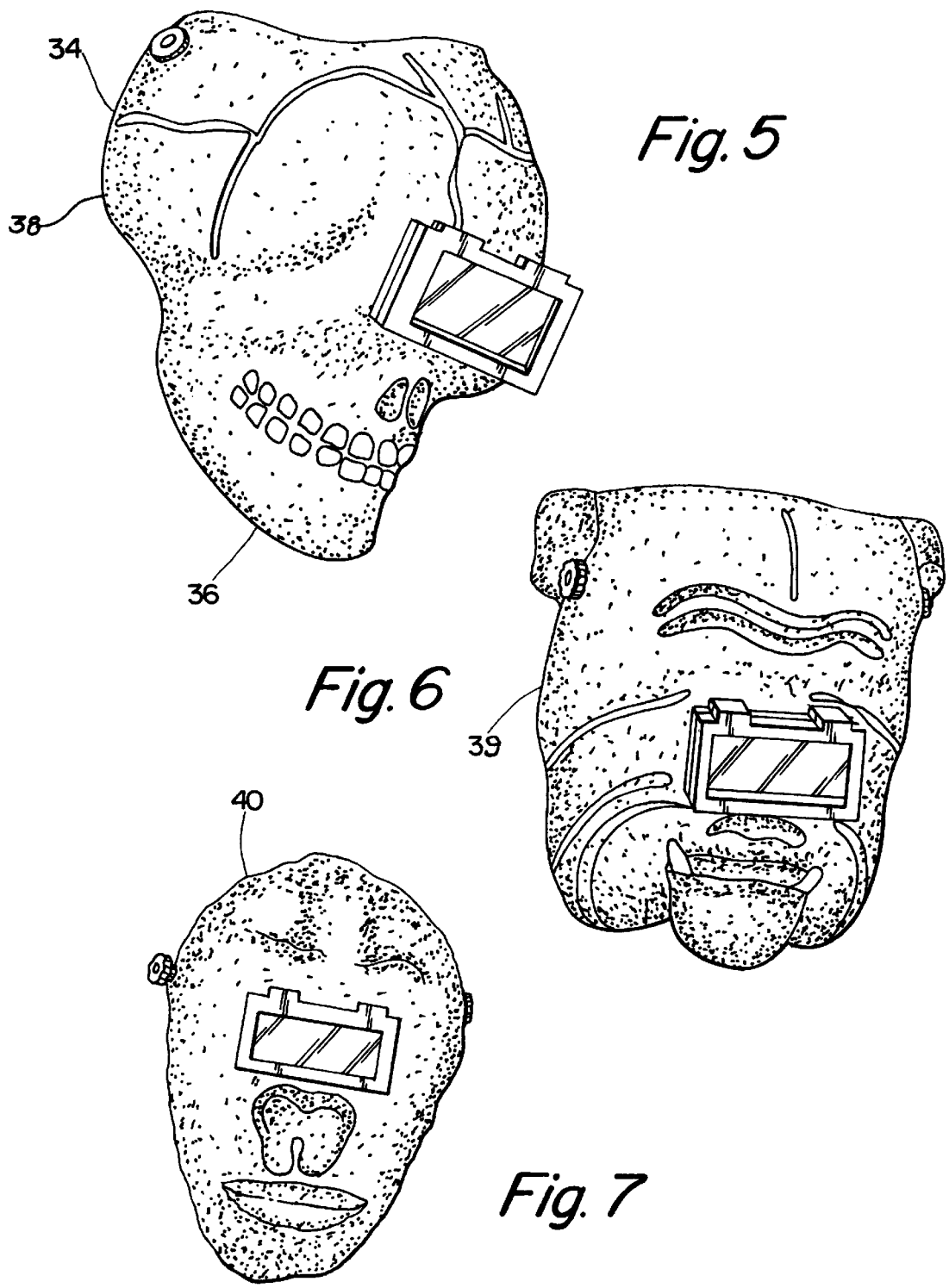

WELDING HELMET

FIELD OF THE INVENTION

This invention relates to welding helmets.

BACKGROUND

Welding helmets generally have a smoothly shaped exterior based on their requisite function to protect the welder's head and neck from sparks. Welding helmets have a viewing device which protects the welder's eye from sparks and also provides protection from the damaging brightness of the welding.

Welding helmets are equipped to be able to rotate from an in-use position in front of the welder's face to an open position. The assemblies used for this in general are headgear which the welder wears on his head and which pivotally attach to the helmet. One type is made of straps fitting the welder's head and another fits on a hard hat worn by the welder. All welding helmets must pass the ANSI Z87.1 standard.

SUMMARY OF THE INVENTION

The invention is a welding helmet made of an appropriate plastic and molded in to the shape of a mammalian head. Particular implementation includes a human skull, a bulldog, and a gorilla. The mammalian head is designed to provide a bib portion to protect the neck and upper chest area and is designated to extend sufficiently to the rear to protect the side of the head and ears from sparks. Also it is shaped to enable the welder to wear a respirator.

BRIEF DESCRIPTION OF DRAWINGS

This application contains at least one drawing executed in color.

FIG. 1 shows a welding helmet of the prior art.

FIG. 2 shows a generalized outline of a welding helmet of the present invention.

FIG. 3 is a partial section along 3—3 of FIG. 2 showing how a welding helmet of the invention is a set up for a hard hat.

FIG. 4 shows how a welding helmet of the invention is set up for a strap type headgear assembly.

FIG. 5 is a partial sectional view showing shows a particular embodiment in a human skull form.

FIG. 6 shows a particular embodiment in a bulldog face form.

FIG. 7 shows a particular embodiment in a gorilla form.

DETAILED DESCRIPTION

Figure 8:
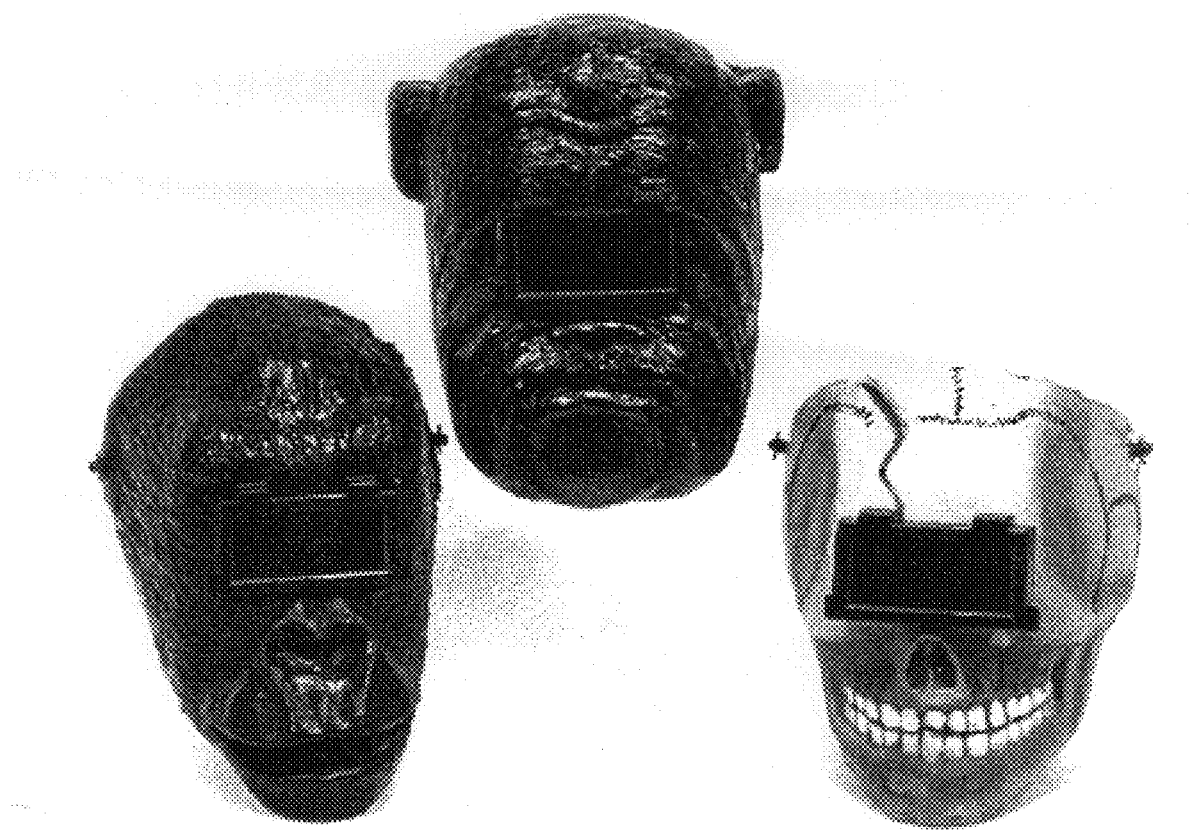
FIG. 8 is a group photograph showing the human skull, bulldog and gorilla welding helmets of FIGS. 5, 6 and 7.

FIG. 1 shows a typical welding helmet 10 of the prior art which has a helmet portion 12, a lens system 14, and pivotable headgear assembly 16 (most of which is not seen). A group of commercially available welding helmets can be found in the 1993 Granger General Catalogue No. 383 at page 1777. Welding helmets are made with a lens system. Sometimes a single lens is built into the helmet. In other models the helmet is adapted to have attached to it a lens retention system made by another manufacturer. These allow exchanging of the lens. A variety of these are seen in the Granger Catalogue.

Welding helmets are also made to accept various headgear assemblies to enable the welder to mount the helmet on his head or on his hard hat, and to allow it to rotate from an in-use position in front of his face to an open position generally over his head. Headgear assemblies made by Huntsman Welding Corp. will work.

One issue in the design and use of welding helmets is to protect the welder's neck and upper chest area from sparks. Therefore some accommodation is made to have the helmet rest or seal against the upper chest such as with a bib portion. Also, welders need protection at the side of their face, even as far back as the ears. This is especially the case where the welder has to maneuver around his work, such as to get his head under a pipe. Therefore the helmet should extend sufficiently to the rear of each side of the welder's head to avoid sparks.

Also, in many cases the welder should wear a respirator while welding.

Therefore the welding helmet must be constructed to accomplish all these requirements.

Consequently the construction of the welding helmets of the present invention are particularly designed to accomplish these requirements.

FIG. 2 shows a generalized welding helmet 18 of the present invention having an exterior surface area 20 to be molded as a mammalian head. It is equipped with a lens 14 and a pivotable headgear assembly 16.

FIG. 3 shows how the welding helmet 18 of the present invention is adapted for a pivotable headgear 22 for use with a hard hat 24. It is not necessary nor intended to show the prior art assemblies in detail. It is sufficient to point out that the welding helmet 18 of the present invention has holes 26A and 26B to receive the parts of a headgear assembly 16 which attaches to a hard hat 18. This mounting of the headgear assembly is generally adaptable for all versions of the mammalian heads, but FIG. 3 shows the human skull version 34.

FIG. 4 shows the welding helmet 18 of the present invention as adapted for conventional headgear of the drop-down limit type which sets the rotation to stop at the right position avoiding the helmet crashing into the welder's chest when it rotates into the in-use. Only one side is shown, the other being a mirror image. The welding helmet 18 has a boss 28 molded into it, or attached, with holes 30 through which the headgear assembly 32 (shown in partial exploded detail) is mounted through the holes 30 to receive the parts of a headgear assembly 20.

Most welding helmets come as purchased with a headgear assembly, but the headgear assembly can be purchased separately and installed in a helmet.

Figure 9:
FIG. 9 is a group photograph showing the human skull, bulldog and gorilla welding helmets of FIGS. 5, 6, 7 and 8 being worn by welders.

FIGS. 5, 8 and 9 shows one embodiment having a human skull shape 34. It is noted that the skull jaw portion 36 extends as a bib would to provide the protection of the neck and upper chest. It also has the portion 38 extending along the side of the head for protection. The skull jaw portion 36 allows a respirator to be worn by the welder.

FIGS. 6, 8 and 9 show the present invention in the form of a bulldog 38. It has all the same features as the human skull of FIGS. 5, 8 and 9.

FIGS. 7, 8 and 9 show the present invention in the form of a gorilla head 40. It has all the same features as the human skull and bulldog of FIGS. 5, 6, 8 and 9.

Although particular embodiments of the invention have been described and illustrated herein, it is recognized that modifications and variations may readily occur to those skilled in the art, and consequently it is intended that the claims be interpreted to cover such modifications and equivalents.

What is claimed is:

1. A welding helmet comprising;
a face protection portion molded of plastic having an exterior shape in the simulative form of the facial portion of a selected non-human mammalian head having a nose feature and a mouth feature and in which there is a welding helmet lens in the area that would contain eye facial features.

2. The welding helmet of claim 1 further comprising;
a headgear assembly pivotably attached to the face protection portion.

3. The welding helmet of claim 2 wherein the headgear assembly is adapted to attach to a hard hat.

4. The welding helmet of claim 2 wherein the headgear assembly is adapted to be worn on a user's head.

5. The welding helmet of claim 1 further comprising a lens retention device permanently attached to the mammalian head in the position, and instead of eye structure of the mammalian head.

6. The welding helmet of claim 1 wherein the mammalian head is a bulldog head.

7. The welding helmet of claim 1 wherein the mammalian head is a gorilla head.

8. A method of making a welding helmet having selected non-human mammalian facial features comprising;
preparing a mold for molding the welding helmet having a reverse structure of the mammalian facial features which features included a nose feature and a mouth feature and in which there is a molded formation for receiving a welding helmet lens in the area that would otherwise contain eye facial features;
molding a plastic material in the mold to create a welding helmet having the selected mammalian facial features on the exterior; and
fitting a welding helmet lens to the welding helmet in the molded formation for a welding helmet lens.

* * * * *